US007037525B2

(12) United States Patent
Schlütermann

(10) Patent No.: US 7,037,525 B2
(45) Date of Patent: May 2, 2006

(54) OXACARBAZEPINE FILM-COATED TABLETS

(75) Inventor: Burkhard Schlütermann, Au (DE)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/429,634

(22) Filed: May 5, 2003

(65) Prior Publication Data

US 2003/0190361 A1 Oct. 9, 2003

Related U.S. Application Data

(63) Continuation of application No. 09/947,574, filed on Sep. 6, 2001, now abandoned, which is a continuation of application No. 09/367,361, filed as application No. PCT/EP98/00794 on Feb. 12, 1998.

(30) Foreign Application Priority Data

Feb. 14, 1997 (CH) ................................. 97/331

(51) Int. Cl.
*A61K 9/14* (2006.01)
*A61K 9/28* (2006.01)

(52) U.S. Cl. ................ 424/474; 424/475; 424/489; 424/465; 514/951

(58) Field of Classification Search ................ 424/464, 424/465, 474, 475, 489, 479, 480, 490, 493, 424/494, 461, 463
See application file for complete search history.

(56) References Cited

U.S. PATENT DOCUMENTS

| | | | | |
|---|---|---|---|---|
| 3,716,640 | A | * 2/1973 | Schindler | ............ 514/217 |
| 4,409,212 | A | 10/1983 | Mondadori | |
| 4,452,738 | A | 6/1984 | Aufderhaar | |
| 4,609,675 | A | 9/1986 | Franz | |
| 4,857,336 | A | 8/1989 | Khanna et al. | |
| 4,897,270 | A | 1/1990 | Deutsch et al. | |
| 4,945,149 | A | 7/1990 | Matsumoto et al. | |
| 5,231,089 | A | 7/1993 | Bodor | |
| 5,472,714 | A | * 12/1995 | Bourquin | |
| 5,476,654 | A | 12/1995 | Conte et al. | |
| 5,840,335 | A | 11/1998 | Wenzel et al. | |
| 5,980,942 | A | 11/1999 | Katzhendler et al. | |
| 6,296,873 | B1 | 10/2001 | Katzhendler et al. | |

FOREIGN PATENT DOCUMENTS

| | | |
|---|---|---|
| EP | 0 435 826 | 12/1990 |
| EP | 0 646 374 A | 4/1995 |
| GB | 835956 | 5/1960 |
| GB | 907309 | 10/1962 |
| GB | 1310120 A | 3/1970 |
| GB | 2 195 248 | 4/1988 |
| IE | 904685 | 12/1996 |
| WO | 8-505379 | 1/1994 |
| WO | WO 94/13298 | 6/1994 |
| WO | WO 94/20110 | 9/1994 |
| WO | 95/29665 | 11/1995 |
| WO | 01/32183 | 5/2001 |

OTHER PUBLICATIONS

* "Oxcarbazephine approved for partial seizures," American Journal of Health–System Pharmacy, vol. 57(5), pp. 414–417, 1 (2000).
* Appel L. E. et al., "Formulation and Optimization of a Modified Microporous Cellulose Acetate Latex Coating for Osmotic Pumps," Pharmaceutical Research, vol. 9, No. 12, pp. 1664–1667 (1992).
* Bodmeier R. et al., "Constant Potassium Chloride Release from Microporous Membraone–Coated Tablets Prepared with Aqueous Colloidal Polymer Dispersions," Pharmaceutical Research, vol. 8, No. 3 (1991).
* CA129:180164, Schlutermann, WO9835681, abstract.
* Degen, P.H. et al., "The Influence of Food on the Disposition of the Antiepileptic Oxcarbazepine and its Major Metabolities in Healthy Volunteers," Biopharmaceutics & Drug Disposition, vol. 15(6), pp. 519–526, (1994).
* Fassihi A.R. et al., "Dissolution of Theophylline from Film–coated Slow Release Mini–tablets in Various Dissolution Media," J. Pharm. Pharmacol., vol. 41, pp. 369–372 (1989).
* Heli Jung et al., "Influence of food on bioavailability of carbazepine," Pharmaceutical Research, vol. 11(10) Supl,, p. s219 (1994).
* Lindholm T. et al., "Polysorbate 20 as a drug release regulator in ethyl cellulose film coatings," J. Pharm. Pharmacol. vol. 38, pp. 686–688 (1986).
* McLean M.J., "Oxcarbazepine: Mechanisms of Action," Epilepsia, vol. 35, S5–S9 (1994).
* Parikh N.H. et al., "Aqueous Ethylcellulose Dispersion of Ethylcellulose. I. Evaluation of Coating Process Variables," Pharmaceutical Research, vol. 10, No. 4, pp. 525–534 (1993).
* Porter S.C. et al., "The permeability of enteric coatings and the dissolution rates of coated tablets," J. Pharm. Pharmacol., vol. 34, pp. 5–8 (1982).
* Schwabe S., "Clinical Development Outlook of Oxcarbazepine," Epilepsia, vol. 35, S2–S4 (1994).
Nurnberg E. et al., Methoden, Springer–Verlag, 1990, Chapt. 3, "Verarbeitung von Stoffen," pp. 534–549.
O'Connor R.E., et al., "Powders," Chapter 88, pp. 1615–1632 (1985).

(Continued)

Primary Examiner—Thurman K. Page
Assistant Examiner—Pili A. Hawes
(74) Attorney, Agent, or Firm—Peter J. Waibel; E Jay Wilusz, Jr.

(57) ABSTRACT

The invention relates to formulations, e.g. film-coated tablets containing oxcarbazepine and to processes for the production of said formulations. The film-coated tablets have a tablet core comprising a therapeutically effective dose of oxcarbazepine being in a finely ground form having a mean particle size of from 4 to 12 μm (median value), and a hydrophilic permeable outer coating.

10 Claims, No Drawings

OTHER PUBLICATIONS

M. Gibaldi, Biopharmaceuticals and Clinical Pharmacokinetics, 4th Edition, Lea & Febiger, Philadelphia, p. 51, (1991).

G.S. Banker, C.T. Rhodes, Marcel Dekker, Modern Pharmaceuticals, pp. 133, 335, 336, 3rd Edition, New York, (1995).

Remington, "The Science and Practice of Pharmacy", 19th Edition, pp. 1449, (1995).

Extract from M-Tec website, no date.

SPC for Trileptal Available from the eMC, no date.

N. Kitamori, "Effect of Drug Content and Drug Particle Size on the Change in Particle Size During Tablet Compression", J. Pharm. Pharmacol. vol. 31, pp. 505–507, (1979).

S.H. Yalkowasky, S. Bolton, "Particle size and Content Uniformity", Pharmaceutical Research vol. 7, pp. 962–966, no date.

M. Dam et al. Euro. J. of Clin. Pharmacol, vol. 2, pp. 59–64, (1981).

M. Dam and P. Jensen, Antiepileptic Drugs, 3rd Edition, Chapter 66, pp. 913–924, (1989).

Raj Suryanarayanan, Powder Diffraction, vol. 5, No. 3, pp. 155–159, (1990).

Noyes and Whitney, JACS, vol. 19, pp. 930–932, (1897).

Translation of the relevant parts of Rudolf Voigt, Lehrbuch der pharmazeutischen Technoloige, 6th Edition, pp. 635–638.

Trileptal Basic Drug Information Issued Mar. 24, 1993.

Report B 84/ 1989 "GP 47 680, Oxcarbazepine" dated Oct. 3, 1989.

Clinical Pharmacology Report No. 47680 02 029 dated Jul. 17, 1998.

Degan et al, "The Influence of Food on the Disposition of the Antiepileptic Oxcabazepine and its Major Metabolites in Healthy Volunteer", Biopharmaceuticals & Drug Disposition, vol. 15, pp. 519–526. (1994).

Heidi Jung, "Influence of Food on Bioavailability of Oxcarbazepine", Abstract.

* cited by examiner

OXACARBAZEPINE FILM-COATED TABLETS

This application is a continuation of application Ser. No. 09/947,574, filed Sep. 6, 2001 now abandoned, which is a continuation of application Ser. No. 09/367,361 filed on Aug. 11, 1999, which is a 371 of PCT/EP98/00794, filed Feb. 12, 1998, which in their entirety are herein incorporated by reference.

The present invention relates to formulations of oxcarbazepine, in particular film-coated tablets and to processes for the production of said formulations.

Oxcarbazepine, 10,11-dihydro-10-oxo-5H-dibenz[b,f] azepine-5-carboxamide, like ®Tegretol [(Novartis) carbamazepine: 5H-dibenz[b,f]azepine-5-carboxamide)], is an agent of first choice in the treatment of convulsions. The known dosage forms, such as tablets and liquid dosage forms, e.g.suspensions, are suitable for ensuring a uniform concentration of active ingredient in the blood, especially in the case of regularly recurring administration over a prolonged period of treatment. Nevertheless, it is always desirable to develop and improve upon existing formulations with respect to, for example bioavailability and compliance.

EP 0 646 374 discloses a formulation of oxcarbazepine which is coated with two layers (an inner and outer layer) containing pigments. The outer layer contains Iron Oxide. The double-coated tablet prevents inhomogeneous colouration of the formulation upon storage.

Despite the known forms of oxcarbazepine, it is always desirable to provide improved formulations.

We have now found formulations of oxcarbazepine which are easily processed into dosage forms and which may enhance the bioavailability of oxcarbazepine and increase compliance.

Accordingly, the invention provides in one of its aspects a formulation of oxacarbazepine comprising oxcarbazepine, preferably in a finely ground form, having a median particle size of approximately 2 to 12 µm, preferably 4 to 12 µm, more preferably 4 to 10 µm and with a maximum residue on a 40 µm sieve of up to 5%, e.g. 2%.

The formulation according to the invention may contain pharmaceutically acceptable excipients commonly used in pharmaceutical formulations, e.g. for oral administration.

In a preferred embodiment according to the invention the formulation may be in the form of a film-coated tablet which comprises,
a) a tablet core comprising a therapeutically effective dose of the oxacarbazepine, preferably in a finely ground form, having a median particle size of approximately from 2 to 12 µm, preferably 4 to 12 µm, more preferably 4 to 10 µm with a maximum residue on a 40 µm sieve of up to 5%, e.g. 2%, and further excipients that are suitable for the production of granules; and
b) a hydrophilic permeable outer coating.

The formulations, e.g. film-coated tablets according to the present invention use oxcarbazepine of fine particle size and narrow particle size distribution and as such may be formulated into dosage forms, e.g solid oral dosage forms such as tablets with relative ease. Furthermore, the fine particle size and narrow particle size distribution may also be beneficial in improving the bioavailablity of oxacarbazepine. Still further the formulations meet all customary requirements, such as storage stability and colour stability.

The colour stability may be achieved using only a single coating containing pigments rather than requiring a double coating containing pigments. This has the advantage of rendering the process of formulating the dosage forms relatively simple and efficient. Furthermore, for a given dosage size, e.g. 300 mg lower amounts of pigment, e.g. Iron oxide (when employed) are required in the coating.

The invention provides in another of its aspects a process for the production of a film-coated tablet containing oxcarbazepine comprising the steps of forming the oxcarbazepine, having a median particle size of approximately from, 2 to 12 µm, preferably 4 to 12 µm, more preferably 4 to 10 µm with a maximum residue on a 40 µm sieve of up to 5%, e.g. 2%, and optionally other excipients into a central core and coating said core with a hydrophilic permeable outer coating.

In a preferred aspect of the invention there is provided a process for the production of a film-coated tablet containing oxcarbazepine which comprises finely grinding oxcarbazepine to a median particle size of approximately from 2 to 12 µm, preferably 4 to 12 µm, more preferably 4 to 10 µm with a maximum residue on a 40 µm sieve of up to 5%, e.g. 2% and, with the admixture of excipients that are suitable for granulation processes, forming the oxcarbazepine into granules, compressing the granules to form tablet cores using conventional tabletting processes, and providing the cores with a hydrophilic permeable outer coating.

Within the scope of the description of the invention, the terms used hereinbefore and hereinafter are defined as follows:

The term "film-coated tablet" denotes a perorally administrable, single-dose, solid dosage form that can be produced by compressing oxcarbazepine with conventional tabletting excipients to form a tablet core using conventional tabletting processes and subsequently coating the core. The tablet cores can be produced using conventional granulation methods, for example wet or dry granulation, with optional comminution of the granules and with subsequent compression and coating. Granulation methods are described, for example, in *Voigt, loc. cit.*, pages 156–169.

Suitable excipients for the production of granules are, for example pulverulent fillers optionally having flow-conditioning properties, for example talcum, silicon dioxide, for example synthetic amorphous anhydrous silicic acid of the Syloid® type (Grace), for example SYLOID 244 FP, microcrystalline cellulose, for example of the Avicel® type (FMC Corp.), for example of the types AVICEL PH101, 102, 105, RC581 or RC 591, Emcocel® type (Mendell Corp.) or Elcema® type (Degussa); carbohydrates, such as sugars, sugar alcohols, starches or starch derivatives, for example lactose, dextrose, saccharose, glucose, sorbitol, mannitol, xylitol, potato starch, maize starch, rice starch, wheat starch or amylopectin, tricalcium phosphate, calcium hydrogen phosphate or magnesium trisilicate; binders, such as gelatin, tragacanth, agar, alginic acid, cellulose ethers, for example methylcellulose, carboxymethylcellulose or hydroxypropylmethylcellulose, polyethylene glycols or ethylene oxide homopolymers, especially having a degree of polymerisation of approximately from $2.0 \times 10^3$ to $1.0 \times 10^5$ and an approximate molecular weight of about from $1.0 \times 10^5$ to $5.0 \times 10^6$, for example excipients known by the name Polyox® (Union Carbide), polyvinylpyrrolidone or povidones, especially having a mean molecular weight of approximately 1000 and a degree of polymerisation of approximately from 500 to 2500, and also agar or gelatin; surface-active substances, for example anionic surfactants of the alkyl sulfate type, for example sodium, potassium or magnesium n-dodecyl sulfate, n-tetradecyl sulfate, n-hexadecyl sulfate or n-octadecyl sulfate, of the alkyl ether sulfate type, for example sodium, potassium or magnesium n-dodecyloxyethyl sulfate, n-tetradecyloxyethyl sulfate, n-hexadecyloxyethyl sulfate or n-octadecyloxyethyl sulfate, or of the alkanesulfonate type, for example sodium, potassium or magnesium n-dodecanesulfonate, n-tetradecanesulfonate, n-hexadecanesulfonate or n-octadecanesulfonate, or non-ionic surfactants of the fatty acid polyhydroxy alcohol ester type, such as sorbitan monolaurate, monooleate, monostearate or monopalmitate, sorbitan tristearate or trioleate, polyoxyethylene adducts of fatty acid polyhydroxy alcohol esters, such as polyoxyethylene sorbitan monolaurate, monooleate, monostearate, monopalmitate, tristearate or trioleate, polyethylene glycol fatty acid esters, such as polyoxyethyl stearate, polyethylene glycol 400 stearate, polyethylene glycol 2000 stearate, especially ethylene oxide/propylene oxide block polymers of the Pluronics® (BWC) or Synperonic® (ICI) type.

Granules may be produced in a manner known per se, for example using wet granulation methods known for the production of "built-up" granules or "broken-down" granules.

Methods for the formation of built-up granules may operate continuously and comprise, for example simultaneously spraying the granulation mass with granulation solution and drying, for example in a drum granulator, in pan granulators, on disc granulators, in a fluidised bed, by spray-drying or spray-solidifying, or operate discontinuously, for example in a fluidised bed, in a batch mixer or in a spray-drying drum.

Preferred are methods for the production of broken-down granules, which may be carried out discontinuously and in which the granulation mass first forms a wet aggregate with the granulation solution, which aggregate is then comminuted or formed into granules of the desired particle size and the granules then being dried. Suitable equipment for the granulation step are planetary mixers, low and high shear mixers, wet granulation equipment including extruders and spheronisers include, for example, apparatus from the companies Loedige, Glatt, Diosna, Fielder, Collette, Aeschbach, Alexanderwerk, Ytron, Wyss & Probst, Werner & Pfleiderer, HKD, Loser, Fuji, Nica, Caleva and Gabler.

The granulation mass consists of comminuted, preferably ground, oxacarbazepine and the excipients mentioned above, for example pulverulent fillers, such as microcrystalline cellulose of the AVICEL type. AVICEL PH 102 is especially suitable. Depending on the method used, the granulation mass may be in the form of a premix or may be obtained by mixing the oxacarbazepine into one or more excipients or mixing the excipients into the oxacarbazepine. The wet granules are preferably dried, for example in the described manner by tray drying or in a fluidised bed.

According to an alternative process variant, tablet cores are produced using the so-called compacting or dry granulation method in which the active ingredient is compressed with the excipients to form relatively large mouldings, for example slugs or ribbons, which are comminuted by grinding, and the ground material is compressed to form tablet cores.

Suitable excipients for the compacting method are preferably those which are suitable for the conventional direct compression methods, for example dry binders, such as starches, for example potato, wheat and maize starch, microcrystalline cellulose, for example commercial products available under the trademarks Avicel®, Filtrak®, Heweten® or Pharmacel®, highly dispersed silicon dioxide, for example Aerosil®, mannitol, lactose, and also polyethylene glycol, especially having a molecular weight of from 4000 to 6000, crosslinked polyvinylpyrrolidone (Polyplasdone® XL or Kollidon® CL), crosslinked carboxymethylcellulose (Acdisol® CMC-XL), carboxymethylcellulose [Nymcel®, for example ZSB-10, (Nyma)], hydroxypropylmethylcellulose, for example the quality HPMC 603, carboxymethyl starch [Explotab® (Mendell) or Primojel® (Scholtens)], microcrystalline cellulose, for example Avicel® PH 102, dicalcium phosphate, for example Emcompress® or talcum. The addition of small amounts of, for example, lubricants, such as magnesium stearate, is also advantageous.

Compression to form tablet cores may be carried out in conventional tabletting machines, for example EK-0 Korsch eccentric tabletting machines or rotary tabletting machines. The tablet cores may be of various shapes, for example round, oval, oblong, cylindrical etc., and various sizes, depending on the amount of oxacarbazepine.

Oxacarbazepine is known. Its manufacture and therapeutic use as an anticonvulsive are described in German Auslegeschrift 2 011 087 which is incorporated herein by reference. A commercially advantageous process for the preparation of that active ingredient is described in European Patent Application No. 0 028 028 which is incorporated herein by reference. Commercially available dosage forms are provided for peroral administration, for example tablets comprising 300 and 600 mg of active ingredient. Those dosage forms are known by the trademark ®Trileptal (Novartis) and have been introduced in a large number of countries, such as Denmark, Finland, Austria and Belgium.

The median particle size of the oxacarbazepine is approximately from 2 to 12 µm, preferably 4 to 12 µm, more preferably 4 to 10 µm with a maximum residue on a 40 µm sieve of up to 5%, e.g. 2%. In a preferred form of process, the median particle size of the oxacarbazepine is approximately from 4 to 12 µm, typically 6 to 8 µm with a maximum residue on a 40 µm sieve of up to 5%, e.g. 2%.

The known particle size analysis methods are suitable for determining the median particle size, for example particle size measurement using light, for example light-scattering methods or turbidimetric methods, sedimentation methods, for example pipette analysis using an Andreassen pipette, sedimentation scales, photosedimentometers or sedimentation in a centrifugal force field, pulse methods, for example using a Coulter counter, or sorting by means of gravitational or centrifugal force. Those methods are described, inter alia, in *Voigt, loc. cit.,* pages 64–79.

In order to produce oxacarbazepine particles, e.g. crystals having the desired particle size, conventional comminution and de-agglomeration techniques may be used, for example grinding in an air-jet mill or impact mill, a ball mill, vibration mill, mortar mill or pin mill.

The hydrophilic permeable outer coating b) comprises a film-forming material that is permeable to water and intestinal juice and that may be swellable, and is soluble or at least to some extent soluble, in those fluids.

Water-permeable film-forming materials are, for example, hydrophilic mixtures of polyvinylpyrrolidone or of a copolymer of polyvinylpyrrolidone and polyvinyl acetate with hydroxypropylmethylcellulose, mixtures of shellac with hydroxypropylmethylcellulose, polyvinyl acetate or copolymers thereof with polyvinylpyrrolidone, or mixtures of water-soluble cellulose derivatives, such as hydroxypropylmethylcellulose, and water-insoluble ethylcellulose.

The coating compositions may, if desired, be used in admixture with other additional excipients, such as talcum or silicon dioxide, for example synthetic amorphous silicic acid of the Syloid® type (Grace), for example SYLOID 244 FP, or wetting agents, for example sorbates or plasticisers, for example the afore-mentioned polyethylene glycols.

Elastic, film-like materials are especially hydrophilic, partially etherified cellulose derivatives.

Hydrophilic, partially etherified cellulose derivatives are, for example, lower alkyl ethers of cellulose having an average degree of molar substitution (MS) that is higher than one and lower than three and an average degree of polymerisation of approximately from 100 to 5000.

The degree of substitution is a measure of the substitution of the hydroxy groups by lower alkoxy groups per glucose unit. The average degree of molar substitution (MS) is an averaged value and indicates the number of lower alkoxy groups per glucose unit in the polymer.

The average degree of polymerisation (DP) is also an averaged value and indicates the average number of glucose units in the cellulose polymer.

Lower alkyl ethers of cellulose are, for example, cellulose derivatives that are substituted at the hydroxymethyl group (primary hydroxy group) of the glucose unit forming the cellulose chains and, where appropriate, at the second and third secondary hydroxy group by $C_1$–$C_4$alkyl groups, especially methyl or ethyl, or by substituted $C_1$–$C_4$alkyl groups, for example 2-hydroxyethyl, 3-hydroxy-n-propyl, carboxymethyl or 2-carboxyethyl.

Suitable lower alkyl ethers of cellulose are preferably cellulose derivatives that are substituted at the hydroxymethyl group (primary hydroxy group) of the glucose unit by the mentioned $C_1$–$C_4$alkyl groups or by substituted $C_1$–$C_4$alkyl groups and at the second and, where appropriate, third secondary hydroxy group by methyl or ethyl groups. Suitable lower alkyl ethers of cellulose are especially methylcellulose, ethylcellulose, methylhydroxyethylcellulose, methylhydroxypropylcellulose, ethylhydroxyethylcellulose, hydroxyethylcellulose, hydroxypropylcellulose, carboxymethylcellulose (in salt form, for example in sodium salt form) or methylcarboxymethylcellulose (also in salt form, for example sodium salt form).

Preferred lower alkyl ethers of cellulose are ethylcellulose (DP: approximately from 150 to 1000, MS: approximately from 1.2 to 1.8), for example of the Aquacoat® type (FMC Corp.), hydroxyethylcellulose (DP: approximately from 120 to 1200, MS: approximately from 1.2 to 2.5) and hydroxypropylcellulose (DP: approximately from 200 to 3000, MS: approximately from 1.0 to 3.0).

Water-permeable film-forming materials also include cellulose acetate trimellitate (CAT), and methacrylic acid/methacrylate 1:1 or 1:2 copolymer, for example EUDRAGIT L and S, for example EUDRAGIT L 12.5 or S 12.5.

The film-forming material may be sprayed on in the form of an aqueous dispersion of redispersible cellulose acetate phthalate—CAP—(Aquateric®: FMC), of polyvinyl acetate phthalate—PVAP—(Coateric®: Colorcon), of hydroxypropylmethylcellulose phthalate—HPMCP—(Aquacoat® HP 50 or HP 55: Shin-Etsu) or also, especially, of acrylic acid/methacrylic acid copolymer partially esterified by $C_1$–$C_4$alkyl groups.

Also suitable is an acrylic acid/methacrylic acid 1:1 copolymer partially esterified by methyl and/or ethyl groups of the type EUDRAGIT L 30 D or water-dispersed EUDRAGIT L 100-55.

The film-forming materials may comprise additional excipients, such as, for example, plasticisers, for example triethyl citrate, for example Citroflex® (Pfizer), triacetin, various phthalates, for example diethyl or dibutyl phthalate, mixed mono- or di-glycerides of the Myvacet® type (Eastman), for example MYVACET 9-40, the polyethylene glycols mentioned hereinbefore, for example having a molecular weight of approximately from 6000 to 8000, and also ethylene oxide/propylene oxide block copolymers of the Pluronic® (BASF) or Synperonic® (ICI) type, pulverulent mould release agents, for example magnesium trisilicate, starch or synthetic amorphous silicic acid of the SYLOID type, for example SYLOID 244 FP.

The hydrophilic permeable outer coating b) comprises white pigments, for example titanium dioxide pigments, preferably combined with iron oxide pigments. The iron oxide may be ferric or ferrous iron oxide, preferably $Fe_2O_3$ optionally in hydrated form. When iron oxide is employed, the amounts employed in the coating will depend upon the size of the particular dosage form. Preferably, the amount of iron oxide employed may be chosen from about 0.1 mg per dosage form, e.g. tablet, to 1.6 mg per dosage form, e.g. tablet, more preferably 0.3 mg per dosage form, e.g. tablet to 0.9 mg per dosage form, e.g. tablet.

The tablet cores may be coated with the hydrophilic permeable coating composition in a manner known per se, using conventional coating methods.

For example, the coating composition is dissolved or suspended in water in the desired quantity ratio. If desired, excipients, such as polyethylene glycol, are added. The solution or dispersion is sprayed onto the tablet cores together with other excipients, for example talcum or silicon dioxide, for example SYLOID 244 FP, for example using known methods, such as spray-coating in a fluidised bed, for example using the Aeromatic, Glatt, Wurster or Hüttlin (ball coater) system, or also in a coating-pan in accordance with the methods known by the names Accela Cota or immersion coating.

Preferably, an aqueous dispersion comprising hydroxypropylmethylcellulose (cellulose HPMC) and pigments is sprayed on.

The formulations, e.g. film-coated tablets according to the invention are useful for their anticonvulsive action and are useful as monotherapy or as adjunctive therapy in the control, prevention or treatment of seizure, e.g. resulting from the onset of epilepsy, status epilepticus, cerebrovascular disorders, head injury and alcohol withdrawal.

The exact dose of oxacarbazepine and the particular formulation to be administered depend upon a number of factors, e.g. the condition to be treated, the desired duration of treatment and the rate of release of the oxacarbazepine. For example, the amount of oxacarbazepine required and the release rate thereof may be determined by in vitro or in vivo techniques, determining how long a particular active agent concentration in the blood plasma remains at an acceptable level for a therapeutic effect.

Preferred regimes include for monotherapy, 150 to 600 mg, e.g 300 mg twice per day. Doses of from 1200 to 2400 mg/day may be tolerated. Preferred regimes for adjunctive therapy include a starting dose of 300 mg/day. Doses from 600 to 2400 mg/day may be tolerated.

The following Examples illustrate the invention.

EXAMPLE 1

| Example 1 | Formulations (mg) | (mg) | (mg) |
|---|---|---|---|
| Tablet Core: | | | |
| Oxcarbazepine | 150 | 300 | 600 |
| Avicel PH 102 | 32.8 | 65.6 | 131.2 |
| Cellulose HPM 603 | 4.2 | 8.4 | 16.8 |
| Polyvinylpyrrolidone | 10 | 20 | 40 |
| Aerosil 200 | 0.8 | 1.6 | 3.2 |
| Magnesium stearate | 2.2 | 4.4 | 8.8 |
| | 200 | 400 | 800 |
| Coating: | | | |
| Polyethylene glycol (PEG) 8000 | 0.832 | 1.331 | 2.162 |
| Cellulose HPM 603 | 4.595 | 7.352 | 11.947 |
| Talcum | 3.327 | 5.323 | 8.649 |
| Titanium Dioxide | 0.935 | 1.496 | 2.431 |
| Iron oxide, yellow | 0.312 | 0.499 | 0.81 |
| | 10 | 16 | 26 |
| Total | 210 | 416 | 826 |

Mix the TRILEPTAL, cellulose HPM 603 (binder) and AVICEL PH 102 (binder, filler, disintegration-promoting excipient) in a mixer, preferably in a high-speed mixer (DIOSNA, LOEDIGE, FIELDER, GLATT etc.). Add water as granulation liquid to the mixture, and knead in a mixer, preferably a high-speed mixer, until an adequate consistency is achieved. Alternatively, the binder cellulose HPM may be dissolved in the granulation liquid, water, beforehand. Granulate the wet granules using a suitable device (ALEXANDER Reibschnitzler, QUADRO-COMILL) and dry in a fluidised bed (AEROMATIC, GLATT). Add AVICEL PH 102, AEROSIL 200 (flow conditioner) and polyvinylpyrrolidone PXL (disintegrator) to the dry granules and comminute and mix in a comminuter (FREWITT, QUADRO-COMILL, FITZMILL). Finally, add magnesium stearate (lubricant) and mix (STOECKLIN container mixer, VRIECO mixer). Alternatively, the lubricant may be added directly to the comminuted material. Compress the final mixture to form TRILEPTAL tablets (eccentric press, rotary press: KILIAN, KORSCH, FETTE, MANESTY).

Coat the tablets with an aqueous preparation consisting of cellulose HPM 603 (film former), iron oxide yellow 17268 (pigment), PEG 8000 (plasticiser for the film former), talcum (anti-adhesive agent, covering agent) and titanium dioxide (covering agent) in a rotating coating pan (ACCELA-COTA, GLATT, DRIACOATER, DUMOULIN). Alternatively, it is possible to use, for example, fluidised-bed or air-suspension apparatus for the coating process (AEROMATIC, GLATT, FREUND, HUETTLIN).

EXAMPLE 2

| | (mg) | (mg) | (mg) |
|---|---|---|---|
| Tablet Core: | | | |
| Oxcarbazepine | 150.0 | 300.0 | 600.0 |
| Avicel PH 102 | 28.8 | 57.5 | 115.0 |
| Cellulose HPM 603 | 5.0 | 10.0 | 20.0 |
| Nymcel ZSB 10 | 13.8 | 27.5 | 55.0 |
| Aerosil 200 | 1.3 | 2.5 | 5.0 |
| Magnesium Stearate | 2.3 | 4.5 | 9.0 |
| Total: | 201.0 | 402.0 | 804.0 |
| Coating: | | | |
| Polyethylene glycol (PEG) 8000 | 0.915 | 1.497 | 2.328 |
| Cellulose HPM 603 | 5.054 | 8.269 | 12.865 |
| Talcum | 3.659 | 5.988 | 9.314 |
| Titanium dioxide | 1.029 | 1.684 | 2.62 |
| Iron oxide, yellow | 0.343 | 0.561 | 0.873 |
| | 11 | 18 | 28 |
| Total | 212.0 | 420.0 | 832.0 |

The oxacarbazepine, cellulose HPM 603 and Avicel PH 102 are mixed together in a planetary mixer (Aeschbach). Alcohol is added to this mixture before it is kneaded in a planetary mixer until a desired consistency is achieved. Thereafter the methodology according to Example 1 is followed to provide coated tablets.

EXAMPLE 3

| | (mg) | (mg) | (mg) |
|---|---|---|---|
| Tablet Core: | | | |
| Oxcarbazepine | 150 | 300 | 600 |
| Avicel PH 102 | 46 | 92 | 184 |
| Cellulose HPM 603 | 6 | 12 | 24 |
| Polyvinylpyrrolidone | 10 | 20 | 40 |
| Aerosil 200 | 0.8 | 1.6 | 3.2 |
| Magnesium stearate | 2.2 | 4.4 | 8.8 |
| Total: | 215 | 430 | 860 |
| Coating: | | | |
| Polyethylene glycol (PEG) 8000 | 0.915 | 1.497 | 2.328 |
| Cellulose HPM 603 | 5.054 | 8.269 | 12.865 |
| Talcum | 3.659 | 5.988 | 9.314 |
| Titanium Dioxide | 1.029 | 1.684 | 2.62 |
| Iron oxide, yellow | 0.343 | 0.561 | 0.873 |
| | 11 | 18 | 28 |
| Total | 226 | 448 | 888 |

The same methodology as Example 1 is carried out on the formulation to provide coated tablets.

What is claimed is:

1. A method of treating seizures, which comprises administering a formulation of oxcarbazepine having improved bioavailability, wherein said oxcarbazepine consists essentially of oxcarbazepine having a maximum residue on a 40 μm sieve of less than or equal to 5%.

2. The method according to claim 1 wherein said maximum residue on a 40 μm sieve is less than or equal to 5%.

3. The method according to claim 1 wherein said formulation is substantially free from particles greater than or equal to 40 μm in size.

4. The method according to claim 1 wherein the seizures results from the onset of epilepsy.

5. A method of treating seizures, comprising oral administration of a formulation of oxacarbazepine, wherein said formulation comprise a therapeutically effective dose of oxacarbazepine and wherein said oxacarbazepine has a median particle size of approximately 2 μm to 12 μm.

6. The method according to claim 5 wherein said oxacarbazepine has a median particle size of approximately 4 μm to 10 μm.

7. The method according to claim 5 wherein said oxacarbazepine has a median particle size of approximately 6 μm to 8 μm.

8. The method according to claim 5 wherein said oxacarbazepine has a maximum residue on a 40 μm sieve of less than or equal to 5%.

9. The method according to claim 5 wherein said oxacarbazepine has a maximum residue on a 40 μm sieve of less than or equal to 2%.

10. The method of claim 1, wherein said oxacarbazepine has a median particle sie of approximately 2 μm to 12 μm.

* * * * *